(12) United States Patent
Pitsis

(10) Patent No.: US 7,832,415 B2
(45) Date of Patent: Nov. 16, 2010

(54) FLOSS GRIP

(76) Inventor: Andrew J. Pitsis, Colonial Mutual Life Building, Suite 1302, Level 1, 14 Martin Place, Sydney, NSW (AU) 2000

(*) Notice: Subject to any disclaimer, the term of this patent is extended or adjusted under 35 U.S.C. 154(b) by 511 days.

(21) Appl. No.: 11/678,325

(22) Filed: Feb. 23, 2007

(65) Prior Publication Data

US 2007/0199576 A1    Aug. 30, 2007

(30) Foreign Application Priority Data

Feb. 24, 2006    (AU) ............................ 2006900927

(51) Int. Cl.
*A61C 15/00*    (2006.01)
(52) U.S. Cl. .................................................. 132/323
(58) Field of Classification Search ......... 132/323–329, 132/309, 311
See application file for complete search history.

(56) References Cited

U.S. PATENT DOCUMENTS

| | | | | |
|---|---|---|---|---|
| 882,204 | A * | 3/1908 | Lassen et al. | 223/99 |
| 912,915 | A * | 2/1909 | Stockland | 223/99 |
| 922,824 | A * | 5/1909 | Tubbs | 132/325 |
| 2,146,375 | A | 2/1939 | Landis | |
| 2,707,782 | A * | 5/1955 | Eby | 132/326 |
| 4,657,034 | A | 4/1987 | Koski | |
| 5,638,841 | A | 6/1997 | Levine | |
| 5,860,434 | A | 1/1999 | Sines | |
| 6,488,036 | B1 * | 12/2002 | Francis | 132/325 |
| 7,328,711 | B2 * | 2/2008 | Hill | 132/323 |

FOREIGN PATENT DOCUMENTS

DE    3911126    10/1990

* cited by examiner

*Primary Examiner*—Robyn Doan
*Assistant Examiner*—Brianne O'Neill
(74) *Attorney, Agent, or Firm*—Molins & Co

(57) ABSTRACT

Disclosed in this specification is a gripping device for dental floss strands, for dental brace wearers. The device comprises a shaft with a bore, a stem that reciprocates in the bore, and optional gripping feature on a distal end of the shaft to facilitate user handling. The stem carries a head through which the dental floss can be inserted. The dental floss is captured between the shaft and the head, eliminating the need for users to hold onto the dental floss manually.

22 Claims, 1 Drawing Sheet

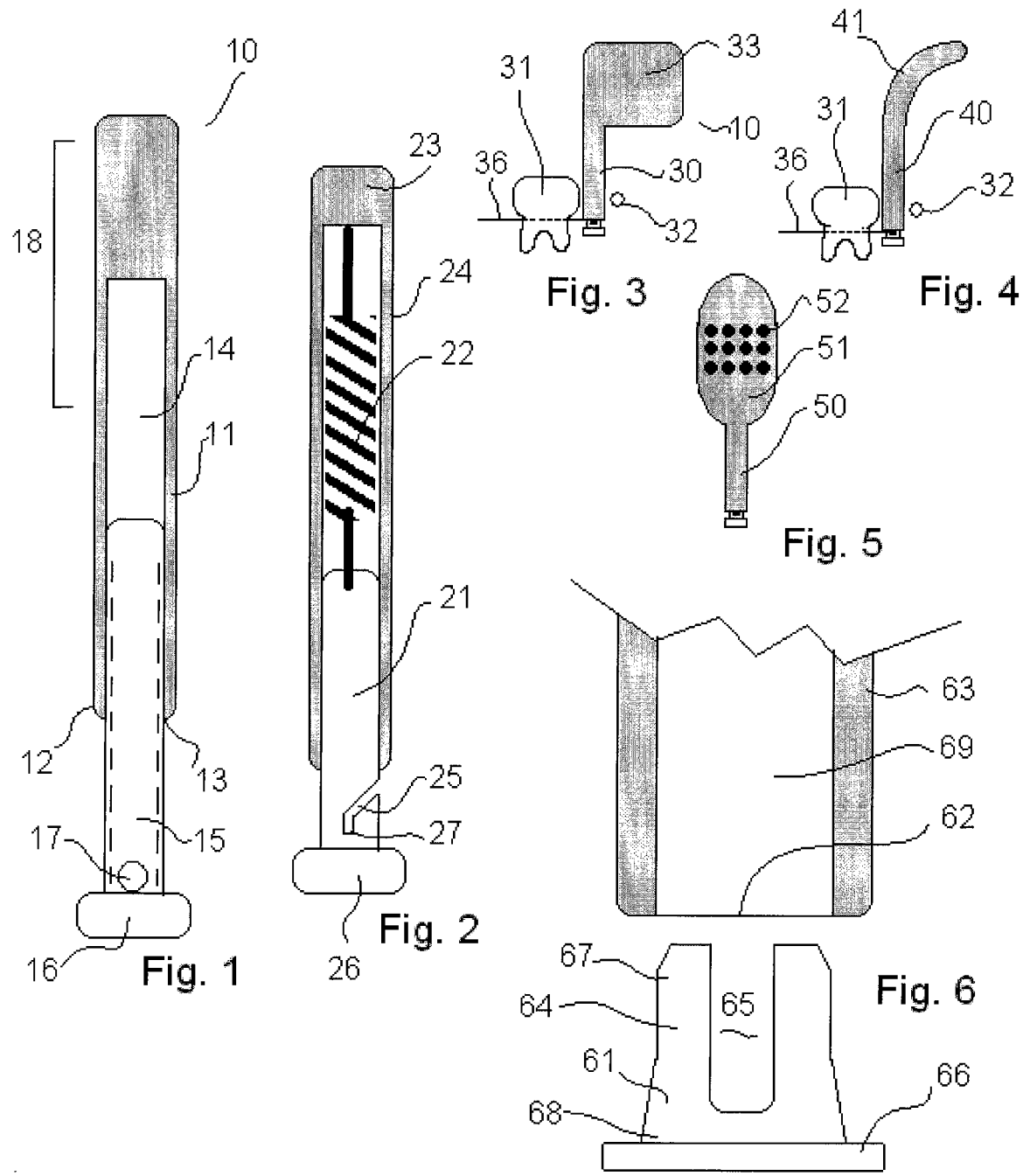

FLOSS GRIP

FIELD OF THE INVENTION

The invention relates to dental hygiene and more particular to a device that a person can use for conveniently gripping dental floss.

BACKGROUND OF THE INVENTION

Orthodontic braces consist of a metal or ceramic bracket attached to each tooth as well as an arch wire that runs from bracket to bracket. The braces exert a constant pressure on the teeth which over time moves teeth into their proper positions. Dental flossing is considered part of a good oral hygiene regiment. Cleaning between the teeth once or twice a day with dental floss removes plaque from between the teeth in areas where a tooth brush can't reach. Flossing is considered essential in preventing periodontal (gum) disease and decay.

Conventional flossing involves, for example, breaking off about 18 inches of floss and winding most of it around one of the middle fingers. The remaining floss is wound around the same finger of the opposite hand. The floss is held tightly between the thumbs and forefingers and guided between the teeth with a general rubbing motion.

The aforementioned method of flossing is impossible for people that wear braces. The presence of the arch wire prevents the floss from reaching the entire interdental gap.

Accordingly, there is required an appliance which is adapted to be inserted between the teeth and the arch wire and that is able to clamp one end of the floss, instead of one of the user's hands.

OBJECTS AND SUMMARY OF THE INVENTION

It is an object of the invention to provide a device for clamping one end of a strand of dental floss, the device adapted to enter the space between a user's teeth and the user's arch wire.

Accordingly, there is provided a grip device comprising a shaft having an end into which is fitted a fastener. In preferred embodiments, the fastener moves with respect to the shaft and is adapted to selectively clamp and retain a strand of dental floss. In particularly preferred embodiments, the opposite end of the shaft further comprises a gripping feature that makes holding the device easier.

BRIEF DESCRIPTION OF THE DRAWING FIGURES

FIG. 1 is a cross section through a gripping device of the present invention;

FIG. 2 is a cross section through another embodiment of a gripping device according to the teachings of the present invention;

FIG. 3 illustrates a further embodiment of the invention in relation to a tooth and an arch wire;

FIG. 4 illustrates a further embodiment of the invention;

FIG. 5 illustrates yet another embodiment of the invention; and

FIG. 6 is a cross section through an alternate fastener.

BEST MODE AND OTHER EMBODIMENTS OF THE INVENTION

As shown in FIG. 1 a gripping device 10 comprises a shaft 11 that is open at one end 12. The opening 13 at that end leads into an internal bore 14. In this example, the bore 14 is closed at one end but optionally, it may be open at both ends. The bore 14 is internally threaded and receives a cooperating threaded stem 15. The stem 15 is shorter than the length of the bore 14 so that it is capable of being threaded into the bore to the point where a head 16 formed at one end of the stem 15 comes into contact with the open end 12 of the gripping device 10. The head 16, which may be smaller than, equal to, or larger than the shaft in size, limits the stem's travel relative to the shaft 11. In preferred embodiments, the head 16 is slightly larger in diameter than the shaft 11. This allows the stem 15 to be conveniently threaded completely into the bore 14 and subsequently removed by rotation in the opposite direction. An opening 17 is provided through the stem 15 adjacent to the head 16. The opening 17 is suitably sized to receive a strand of dental floss.

The device depicted in FIG. 1 is used by inserting one end of a strand of dental floss through the opening 17. The head 16 is then gripped while the shaft 11 is advanced toward the head 16 by rotating it. As the open end 12 makes contact with the head 16 the strand of floss is captured or clamped between the end of the shaft 12 and the head 16 of the stem. In preferred embodiments, at least an upper portion 18 of the shaft 11 is provided with gripping features such as a physical texture, knurling or the like. In this example, the maximum diameter of the device (including the head 16) is between as little as 0.5 and 2.5 mm, preferably about 2 mm. This allows the device to be located between a user's teeth and that user's arch wire.

FIG. 2 illustrates and alternate embodiment of the invention. In this embodiment, the stem 21 is retained by a tension spring or other bias 22 that biases the stem 21 toward the distal end 23 of the device. The tension spring 22 extends between one end of the bore 14 and the stem 21. In this way the threaded engagement between the shaft 24 and the stem 21 is eliminated. In this embodiment, a slot 25 adjacent the head 26 takes the place of the through opening 17 depicted with reference to FIG. 1. The slot 25 is angled toward the head 26 and terminates in a retaining pocket 27 that assists in trapping the floss when the tensioning device 22 draws the head 26 into contact with the lower end of the shaft 24.

As shown in FIG. 3, the shaft 30 of the device 10 is adapted to fit between a user's teeth 31 and the arch wire 32 of their braces. As shown in this example, one end of the shaft 30 expands into a gripping portion 33. In this example, the gripping portion 33 is asymmetrical with respect to the shaft 30 and provides an enlarged area that can be gripped between the thumb and forefinger of a user. Note that the floss 36 can thus enter the interdental space below the level of the arch wire 32.

In the example depicted in FIG. 4, the shaft 40 includes a bent portion 41. In the example depicted in FIG. 5, the shaft 50 terminates in a flat paddle-like gripping portion 51 with optional gripping texture 52 applied to one or both sides of the gripping area 51. It will be appreciated that a wide variety of gripping area types and shaft configurations are contemplated as being within the scope of the present invention.

As shown in FIG. 6, the strand of dental floss may be retained by a press-fit or frictional type clamping fastener 61 that fits into the open end 62 of the shaft 63. In this example, the fastener 61 comprises a body 64 into which is formed the floss retaining slot 65. The body 64 also incorporates a head 66. In preferred embodiments, the head 66 is slightly larger in diameter than the diameter of the shaft 63. Note that the body 64 includes a generally cylindrical portion 67 that tapers outward, increasing slightly in diameter toward its base 68. In this way, the body 64 enters the bore 69 easily but creates an interference fit between the fastener 61 and the shaft the further that the fastener is introduced into the bore 69.

While the present invention has been disclosed with reference to various details of construction, these will be understood as having been provided by way of example and not as limitations to the scope or spirit of the invention. In particular, the retention of the dental floss has been disclosed with reference to a variety of different clamping mechanisms. These mechanisms should be considered as being interchangeable with respect to the various shaft styles and gripping portions disclosed. Further, the particular gripping styles have been provided as particularised examples and should not be considered exhaustive of the types of gripping styles that would be useful in conjunction with the device disclosed herein. It will also be appreciated that although the diameter of the device is practically limited by the requirement that it fit between the tooth and the arch wire, the length of the device is only limited by practicality and user convenience. The device is useful in dental care to people with or without brace.

What is claimed is:

1. A floss grip for use by a user with orthodontic braces bonded to their teeth, the braces being operatively associated with an orthodontic arch wire, the floss grip being adapted to releasably retain an end of a strand of floss, the floss grip consisting essentially of:
   a single unbranched shaft having a distal end and an open end, the open end leading into an internal bore;
   a stem received by the internal bore;
   a head formed on one end of the stem, the head adapted to limit a travel of the stem relative to the shaft; and
   an opening formed into the stem and located adjacent to the head;
   wherein the opening is adapted to receive the end of the strand of floss;
   wherein relative movement of the head toward the distal end of the shaft clamps the strand of floss received by the opening, thereby releasably retaining the strand of floss; and
   wherein, in use, the floss grip can be gripped at the distal end by the user, and the floss grip is sized so that the open end can be located between the arch wire and teeth while retaining the strand of floss.

2. The floss grip of claim 1, wherein,
   a maximum diameter of the floss grip is between 1.5 mm and 2.5 mm.

3. The floss grip of claim 1, wherein,
   the maximum diameter of the floss grip is about 2 mm.

4. The floss grip of claim 1, wherein,
   a diameter of the head is larger than a diameter of the shaft.

5. The floss grip of claim 1, wherein,
   the stem and shaft have cooperating threads.

6. The floss grip of claim 5, wherein,
   the opening formed into the stem is a through opening adapted for a strand of dental floss to be inserted.

7. The floss grip of claim 1, wherein, relative movement of the head toward the distal end of the shaft is operatively associated with a tensioning device located in the bore, the tensioning device providing a bias for retaining the stem toward the distal end of the shaft.

8. The floss grip of claim 7, wherein,
   the tensioning device is a tension spring.

9. The floss grip of claim 1, wherein,
   the opening formed into the stem is a slot that is angled towards the head.

10. The floss grip of claim 9, wherein,
    the slot terminates in a retaining pocket adapted to assist in trapping the floss.

11. The floss grip of claim 1, wherein, floss grip can be gripped by the user proximal to the distal end a gripping portion located on the distal end of the shaft.

12. The floss grip of claim 11, wherein,
    the gripping portion is an enlarged area that is asymmetrical with respect to the shaft.

13. The floss grip of claim 11, wherein,
    the gripping portion is a bent portion.

14. The floss grip of claim 11, wherein,
    a gripping texture is applied to a gripping area of the gripping portion.

15. The floss grip of claim 11, wherein,
    the gripping area is flat and paddle-like.

16. A floss grip for use by a user with orthodontic braces bonded to their teeth, the braces being operatively associated with an orthodontic arch wire the floss grip being adapted to releasably retain an end of a strand of floss, the floss grip consisting essentially of:
    an unbranched shaft having a distal end and an open end, the open end leading into an internal bore;
    a fastener that fits into the open end of the shaft, the fastener comprising a body into which is formed a floss retaining slot;
    wherein the slot is adapted to receive the end of the strand of floss;
    wherein fitting the fastener to the open end of the shaft clamps the strand of floss received by the slot, thereby releasably retaining the strand of floss; and
    wherein, in use, the floss grip can be gripped proximal to the distal end by the user, and the floss grip is sized such that it can be located between the arch wire and teeth while retaining the strand of floss.

17. The floss grip of claim 16, wherein,
    the body incorporates a head, a diameter of the head being larger than a diameter of the shaft.

18. The floss grip of claim 16, wherein,
    the body includes a generally cylindrical, tapered portion that increases in diameter toward a base of the body, for creating an interference fit between the bore and the body.

19. A floss grip for use by a user with orthodontic braces bonded to their teeth, the braces being operatively associated with an orthodontic arch wire, the floss grip being adapted to releasably retain an end of a strand of floss, the floss grip comprising:
    an unbranched shaft having a distal end and an open end, the open end leading into an internal bore;
    a stem received by the internal bore;
    a head formed on one end of the stem, the head adapted to limit a travel of the stem relative to the shaft;
    an opening formed into the stem and located adjacent to the head;
    wherein the opening is adapted to receive the end of the strand of floss;
    wherein relative movement of the head toward the distal end of the shaft clamps the strand of floss received by the opening, thereby releasably retaining the strand of floss;
    wherein, in use, the floss grip can be gripped proximal to the distal end by the user, and the floss grip is sized such that the open end can be located between the arch wire and teeth while retaining the strand of floss;
    wherein floss grip is devoid of a floss reservoir adapted to enable the strand of floss to extend therefrom during use.

20. The floss grip of claim 19, wherein,
    the stem and shaft have cooperating threads.

21. The floss grip of claim 19, further comprising, a tensioning device located in the bore, the tensioning device providing a bias for retaining the stem toward the distal end of the shaft.

22. The floss grip of claim 19, further comprising, a gripping portion located on the distal end of the shaft.